US012635693B2

(12) United States Patent
Sharma

(10) Patent No.: US 12,635,693 B2
(45) Date of Patent: May 26, 2026

(54) ACTIVATED FERRATE COMPOSITIONS AND METHODS

(71) Applicant: THE TEXAS A&M UNIVERSITY SYSTEM, College Station, TX (US)

(72) Inventor: Virender K. Sharma, College Station, TX (US)

(73) Assignee: THE TEXAS A&M UNIVERSITY SYSTEM, College Station, TX (US)

(*) Notice: Subject to any disclaimer, the term of this patent is extended or adjusted under 35 U.S.C. 154(b) by 746 days.

(21) Appl. No.: 17/759,244

(22) PCT Filed: Jan. 21, 2021

(86) PCT No.: PCT/US2021/014436
§ 371 (c)(1),
(2) Date: Jul. 21, 2022

(87) PCT Pub. No.: WO2021/150768
PCT Pub. Date: Jul. 29, 2021

(65) Prior Publication Data
US 2023/0085218 A1 Mar. 16, 2023

Related U.S. Application Data

(60) Provisional application No. 62/964,282, filed on Jan. 22, 2020.

(51) Int. Cl.
| | |
|---|---|
| *A01N 59/16* | (2006.01) |
| *A01P 1/00* | (2006.01) |
| *A61L 2/18* | (2026.01) |
| *C02F 1/50* | (2023.01) |
| *C02F 1/52* | (2023.01) |
| *C02F 1/72* | (2023.01) |
| *A61L 101/28* | (2006.01) |
| *C02F 101/38* | (2006.01) |

(52) U.S. Cl.
CPC ................ *A01N 59/16* (2013.01); *A01P 1/00* (2021.08); *A61L 2/18* (2013.01); *C02F 1/505* (2013.01); *C02F 1/5236* (2013.01); *C02F 1/72* (2013.01); *A61L 2101/28* (2020.08); *C02F 2101/38* (2013.01); *C02F 2303/04* (2013.01)

(58) Field of Classification Search
CPC .............. A01N 59/16; A01P 1/00; A61L 2/18
See application file for complete search history.

(56) References Cited

U.S. PATENT DOCUMENTS

2011/0023913 A1 2/2011 Fulling

FOREIGN PATENT DOCUMENTS

WO WO-2019178529 A1 * 9/2019 ............. A23B 70/10

OTHER PUBLICATIONS

Elhalwagy (Amine-rich polymers for water purification applications, Materials Today Chemistry, 2023) (Year: 2023).*
Zahradníčková (Chiral secondary amino acids, their importance, and methods of analysis, Amino Acids, 2022) (Year: 2022).*
Breibeck, et al. "The polypeptide biophysics of proline/alanine-rich sequences (PAS): Recombinant biopolymers with PEG-like properties." Biopolymers 109.1 (2018): e23069, 12 pages.
International Search Report and Written Opinion mailed May 3, 2021, issued in International Application No. PCT/US2021/014436 filed Jan. 21, 2021, 8 pages.
Manoli, et al. "Enhanced oxidative transformation of organic contaminants by activation of 1-3, 6-9, 20-27 ferrate (VI): Possible involvement of FeV/FeIV species." Chemical Engineering Journal 307: 513-517, Jan. 1, 2017, 17 pages.
Zhang, et al. "Effect of Metal Ions on Oxidation of Micropollutants by Ferrate (VI): Enhancing 1-3, 6-9, 20-27 Role of FeIV Species." Environmental Science & Technology, 55, 623-633, Dec. 16, 2020.

* cited by examiner

*Primary Examiner* — Andrew S Rosenthal
*Assistant Examiner* — Danielle Kim
(74) *Attorney, Agent, or Firm* — Barnes & Thornburg LLP

(57) ABSTRACT

Activated ferrate solutions, methods of their preparation, and methods of disinfecting surfaces and oxidizing pollutants in water are provided.

20 Claims, 5 Drawing Sheets

ACTIVATED FERRATE COMPOSITIONS AND METHODS

CROSS-REFERENCE TO RELATED APPLICATION

This application is a National Stage of International Application No. PCT/US2021/014436, filed Jan. 21, 2021, which claims the benefit of U.S. Provisional Application No. 62/964,282, filed Jan. 22, 2020, the disclosure of each of which is expressly incorporated herein by reference in its entirety.

BACKGROUND

One of the major issues of this century is to provide clean water to humans. According to the United Nations and World Health Organization (WHO), more than 2 billion humans face some kind of risk associated with unsafe drinking water at home. Water pollutants usually contains diseases-causing agents (e.g., protozoa, virus, and bacteria), toxic metals (e.g. arsenic and lead), nutrients (e.g., nitrate and phosphate), and organic pollutants (e.g., surfactants, dyes, and pesticides). Other recent concerns include endocrine disruptor chemicals (EDCs), pharmaceuticals, and personal care products (PCPs). Contaminants present in industrial, agricultural, and consumer products also enter drinking water resources (e.g. surface, groundwater and surface water).

In recent years, tetraoxy iron in +6 oxidation state (Fe-$^{VI}O_4^{2-}$), commonly called "ferrate", has been shown to be potentially effective disinfectant, oxidant, and coagulant for treating water and wastewater. Ferrate reduces to Fe(III), forming no harmful byproducts, and is, therefore, an environmentally friendly compound compared to the unpleasant and harmful by-products formed from conventional chemicals (e.g., chlorine).

Ferrate has ability to inactivate a wide range of microorganisms (e.g., *Escherichia coli, Staphylococcus aureus, Shigella flexneri*, and *Salmonella typhimurium*) at very low concentrations in water. Ferrate has also shown effectiveness in oxidation of low levels of inorganic and organic contaminants and demonstrated capability to remove low levels of phosphate and toxic metals. Though ferrate inactivates microorganisms effectively, the Ct values (where C is concentration of a ferrate and t is the contact time with the water being disinfected) are high due to the duration of contact required to achieve disinfection. In good practice of disinfection, a value of t should be low to achieve required disinfection of water (or inactivation of microorganisms) in a shorter period of time.

Ferrate can oxidize a large number of organic contaminants and thus can be used for their removal from wastewater; however, some of these compounds have been recalcitrant towards ferrate, requiring long oxidation times.

There remains a need for environmentally friendly, comprehensive system that can efficiently disinfect surfaces and purify wastewater.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, provided herein is an activated ferrate composition comprising one or more compounds comprising a secondary amino group and ferrate.

In some embodiments, the composition is an aqueous solution.

In some embodiments, the one or more compounds comprising a secondary amino group is an amino acid comprising a secondary amino group. In some embodiments, the amino acid comprising a secondary amino group is proline. In some embodiments, the one or more compounds comprising a secondary amino group is a polymer. In some embodiments, the polymer is a polypeptide, such as a polypeptide that comprises one or more prolines. In some embodiments, the polymer is an ethylenic backbone polymer comprising side chains comprising secondary amino groups.

In some embodiments, the concentration of ferrate is between about 0.001 wt % and about 5.0 wt %. In some embodiments, the molar ratio of the one or more compounds comprising a secondary amino group to ferrate is from about 0.25 to about 2.0.

In some embodiments, the composition further comprises a disinfectant selected from sodium hypochlorite, chloramine, quaternary alkylamines, and combinations thereof. In some embodiments, the composition further comprises one or more surfactants.

In some embodiments, the activated ferrate composition has a pH between about 5.0 and about 12.0, between about 7.0 and about 12.0, or between about 8.0 and about 10.0.

In another aspect, provided herein is a method of reducing the concentration of one or more contaminants in a contaminated fluid comprising contacting the fluid with the activated ferrate composition of the disclosure. In some embodiments, the activated ferrate composition comprises ferrate and proline.

In some embodiments, the contaminated fluid is wastewater. In some embodiments, the one or more contaminants is a recalcitrant organic compound, a microorganism, or a combination thereof. In some embodiments, the one or more contaminants is *Escherichia coli, Staphylococcus aureus, Shigella flexneri, Salmonella typhimurium, Clostridium difficile* bacteria, *Clostridium difficile* spore, Rhinovirus, Norovirus, Zika virus, Ebola virus, *Aspergillus*, amoeba, helminthic egg, *Histoplasma*, or a combination thereof.

In another aspect, the disclosure provides a method of preparing an activated ferrate solution, comprising contacting ferrate or a ferrate intermediate with an aqueous composition comprising one or more compounds comprising secondary amino group.

In some embodiments, the ferrate intermediate is produced by heating an iron-containing material selected from iron oxides, iron salts, and combinations thereof in the presence of potassium nitrate. In some embodiments, the ferrate intermediate comprises potassium ferrate.

In some embodiments, one or more compounds comprising secondary amino group is proline. In some embodiments, the one or more compounds comprising a secondary amino group is a polymer. In some embodiments, the polymer is a polypeptide. In some embodiments, the polypeptide comprises one or more prolines. In some embodiments, the polymer is an ethylenic backbone polymer comprising one or more side chains comprising one or more secondary amino groups.

In another aspect, the disclosure provides activated ferrate solution prepared by the method disclosed herein.

In another aspect, the disclosure provides a method of disinfecting a surface comprising contacting one or more surfaces with the activated ferrate of the disclosure.

In some embodiments, disinfecting the surface comprises killing one or more antibiotic-resistant microorganisms. In some embodiments, the surface is a health care surface. In some embodiments, the surface comprises a material selected from the group consisting of glass, ceramic, metal, wallpaper, painted walls, and plastic.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

In one aspect, provided herein are activated ferrate compositions capable of efficient removal of organic contaminants from contaminated fluids, such as wastewater, and surface decontamination. The activated ferrate compositions of the disclosure comprise one or more compounds comprising a secondary amino group and ferrate.

As used herein, "ferrate", also referred to interchangeably as $Fe^{VI}O_4{}^{2-}$, $Fe(VI)O_4{}^{2-}$, and "ferrate(VI)" refer to tetraoxy iron in +6 oxidation state with the chemical formula $[FeO_4]^{2-}$ or material comprising an oxycompound of iron in an oxidation state of six.

In certain embodiments, the activated ferrate solutions have a concentration of ferrate from about 0.001 wt % to about 5.0 wt % or from about 0.001 wt % to about 1.0 wt % or. As used herein, the term "about" refers to +/−5% of the recited value. In certain embodiments, the activated ferrate solutions have a concentration of $Fe^{VI}O_4{}2-$ or ferrate of about 5.0 wt %.

The +6 valence of iron is the highest oxidation state accessible and is called ferrate (e.g., $Fe^{VI}O_4{}^{2-}$). Ferrate provides unique opportunities in treating contaminated water by oxidation, disinfection, and coagulation. Ferrate can oxidize a wide range of contaminants and disinfect a large variety of bacteria and viruses in water and wastewater. However, few contaminants of concerns are recalcitrant towards ferrate. For example, Carbamazepine (CBZ) is one such exemplary recalcitrant molecule that resists oxidation by ferrate and requires several hours to be substantially removed by ferrate, especially when the treated sample is under alkaline condition (e.g., urine). Furthermore, the oxidation ability of ferrate is diminished under alkaline pH.

Thus, application of ferrate for various applications in removing contaminants and inactivating microorganisms becomes restricted.

Figure 1:
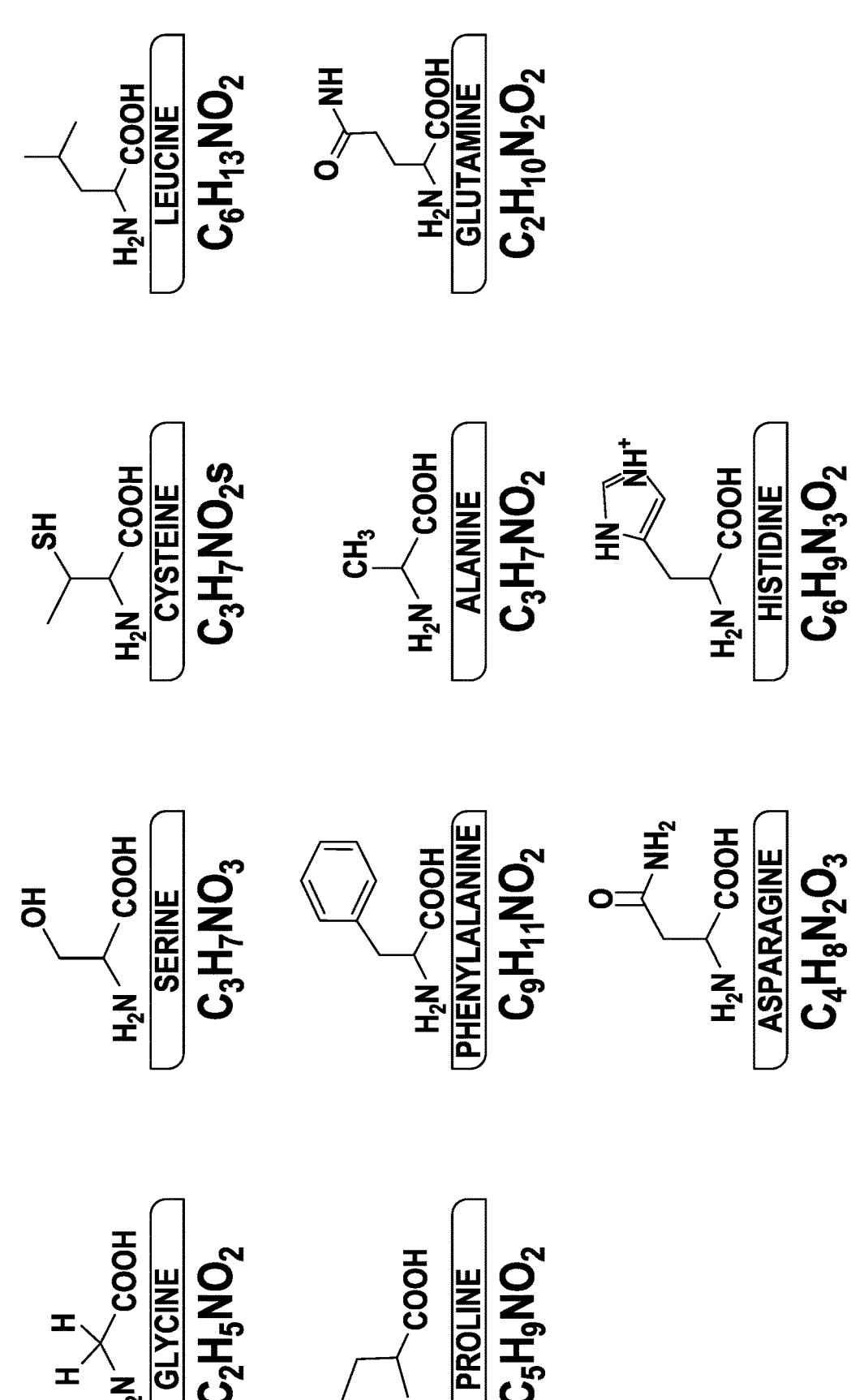
FIG. 1 shows the chemical structures of 10 selected amino acids.

In some embodiments, it is advantageous to increase the activity of ferrate or to produce "activated ferrate," i.e. ferrate that can oxidize recalcitrant contaminants. Without wishing to be bound by theory, to test the hypothesis that +4 and +5 valence of iron (i.e., iron (IV) and iron (V)) may assist in generating activated ferrate, a combination of ferrate with various organic molecules to obtain activated ferrate has been tested. In search for suitable organic molecules, amino acids presented a possibility because of their natural existence and non-toxicity to human and ecological health. Upon testing of ten exemplary amino acids of different structures (FIG. 1), surprisingly, only the compound comprising a secondary amino group, i.e., proline, demonstrated activation of ferrate, as demonstrated by oxidation of CBZ by such activated ferrate solution in 1 min under alkaline pH.

In some embodiments, the activated ferrate compositions of the disclosure comprise one or more compounds comprising a secondary amino group. In some embodiments, the one or more compounds are an amino acid comprising a secondary amino group, for example, proline.

In some embodiments, the molar ratio of the one or more compounds, e.g., amino acids, comprising secondary amino group to ferrate is from about 0.25 to about 2.0. In some embodiments, the concentration of the one or more compounds, e.g., amino acids, comprising secondary amino group in the activated ferrate solutions is from about 0.0001 M to about 1.0 M.

In some embodiments, the activated ferrate compositions disclose herein are aqueous solutions comprising ferrate. In certain embodiments, the solutions comprise water. Any suitable water can be used, including undistilled, non-deionized, tap, distilled, deionized, or DDI water. Potable or non-potable water can be used to prepare the activated ferrate solutions disclosed herein. Regular tap water, e.g., water that has not been distilled or deionized, can be used in preparation of the activated ferrate solutions provided herein, reducing the costs of preparation of the activated ferrate solutions. Alternatively, distilled or deionized water can be used.

In some embodiments, the activated ferrate compositions of the disclosure can further comprise a disinfectant selected from sodium hypochlorite, chloramine, quaternary alkylamines, and combinations thereof. For example, the disinfectant can be sodium hypochlorite present in the activated ferrate solution at a concentration of between about 0.001 wt % and about 1.0 wt %. Additionally, the activated ferrate solutions provided herein can further comprise one or more surfactants.

In some embodiments, the activated ferrate compositions have a pH between about 5.0 and about 12, between about 7.0 and about 12, or between about 8.0 and about 10.

The activated ferrate compositions, e.g., solutions, disclosed herein can be prepared by any suitable method.

In additional aspect, provided herein is a method of preparing an activated ferrate solution, comprising contacting a ferrate intermediate with an aqueous composition comprising one or more compounds comprising a secondary amino group, e.g., proline. In some embodiments, the ferrate intermediate comprises potassium ferrate. In some embodiments, the ferrate intermediate is an iron-containing solid intermediate generated by heating an iron-containing material selected from iron oxides, iron salts, and combinations thereof in the presence of potassium nitrate.

In some embodiments, the method comprises:

(a) heating an iron-containing material selected from iron oxides, iron salts, and combinations thereof in the presence of potassium nitrate, thereby obtaining an iron-containing solid intermediate; and (b) contacting the iron-containing solid intermediate with an aqueous composition comprising one or more compounds comprising secondary amino group.

In some embodiments, the one or more compounds comprising a secondary amino group is a small molecule comprising a secondary amino group. In some embodiments, the one or more compounds comprising a secondary amino group is an amino acid comprising a secondary amino group, e.g., proline. In some embodiments, the one or more compounds comprising a secondary amino group is a polymer, for example, a polypeptide that can comprise one or more prolines.

In some embodiments, the activated ferrate solutions disclosed herein can be prepared by contacting a solution comprising a ferrate intermediate, such as potassium ferrate or the iron-containing solid intermediate described above, with a water-insoluble polymer comprising a plurality of secondary amino groups. Exemplary polymers that can be used in the methods of the disclosure include resins, such as ethylenic backbone polymers comprising one or more side chains comprising one or more secondary amino groups. In some embodiments, a solution comprising the iron-containing solid intermediate can be passed through a bed of water-insoluble polymer comprising a plurality of secondary amino groups thereby activating the ferrate.

In another aspect, the disclosure provides a method of reducing the concentration of one or more contaminants in a contaminated fluid comprising contacting the contaminated fluid with the activated ferrate compositions disclosed herein. In some embodiments, the one or more contaminants is a recalcitrant organic compound, a microorganism, or a combination thereof. Contaminants suitable for removal using the methods disclosed herein include *Escherichia coli, Staphylococcus aureus, Shigella flexneri, Salmonella typhimurium, Clostridium difficile* bacteria, *Clostridium difficile* spores, Rhinovirus, Norovirus, Zika virus, Ebola virus, *Aspergillus*, amoeba, helminthic eggs, *Histoplasma*, or a combination thereof. Fluids that can be decontaminated by the methods disclosed herein include contaminated water, such as industrial wastewater and sewage. A used herein, contaminated water comprises wastewater, polluted water, and water containing organic contaminants such as artificial sweeteners, pesticides, pharmaceuticals, and X-ray contrast media. In some embodiments of the methods of the disclosure, removal of contaminants comprises the chemical removal of organic contaminants by oxidation.

In some embodiments, the contaminant is a recalcitrant contaminant. As used herein, recalcitrant contaminants are contaminants which have shown low oxidative reactivity with a non-activated $Fe^{VI}$ and show incomplete removal from water despite increasing treatment time for removal or increasing concentrations of non-activated ferrate solutions.

In another aspect, the disclosure provides methods of disinfecting a surface, comprising contacting a surface with an activated ferrate solution disclosed herein.

A used herein, disinfecting the surface comprises killing, destroying, inactivating, or otherwise disabling a microorganism such as a bacterium or a virus. As used herein, disinfecting includes killing, inactivating, or otherwise rendering the microorganism incapable of reproducing and/or infecting a host organism, such as a human.

In certain embodiments, disinfecting includes killing one to 100 million organisms. In certain embodiments, the present methods are capable of disinfecting surfaces including about $1*101$ microorganisms/cm$^2$ to about $1*10^8$ microorganisms/cm$^2$. Microorganisms that can be killed or otherwise rendered incapable of reproducing and/or infecting a host organism include bacteria, viruses, fungi, archaea, protozoa, and algae. Representative microorganisms include *Escherichia coli, Staphylococcus aureus, Shigella flexneri, Salmonella typhimurium. Clostridium difficile* bacteria and spores. Rhinovirus, Norovirus, Zika virus, Ebola virus, *Aspergillus*, amoeba, helminthic eggs, and *Histoplasma*.

In certain embodiments, the microorganism is an antibiotic-resistant microorganism. In certain embodiments, the antibiotic-resistant microorganism is methicillin-resistant *Staphylococcus aureus* (MRSA).

Surfaces that can be disinfected include any surface having microorganisms that needs disinfection. Such surfaces include, without limitation, surfaces in homes, schools, hotels, vehicles, offices, businesses, parks, bathrooms, and the like. In certain embodiments, the surfaces are healthcare surfaces present in, for example, hospitals, nursing homes, hospices, out-patient facilities, dentists' offices, pharmacies, and the like. In certain embodiments, the health care surface is selected from a surface of a hospital bed, a hospital floor, non-sterilizable medical equipment, and a tray table.

In certain embodiments, the surface to be disinfected is porous. In certain embodiments, the surface to be disinfected is woven. In certain embodiments, the surface comprises a material selected from glass, ceramic, metal, wall paper, painted walls, and plastic.

In certain embodiments, disinfecting the surface or reducing the concentration of a contaminant reduces the iron in $Fe^{VI}O4^{2-}$ from Fe(VI) to Fe(III) or Fe(II). In certain embodiments, the by-products of disinfecting reactions between activated ferrate and microorganisms are non-toxic or otherwise harmless by-products, such as Fe(III).

EXAMPLES

Preparation of Activated Ferrate Solution.

Activated ferrate was prepared by adding a ferrate intermediate (e.g., potassium ferrate (VI)) directly into water in which one or more activating agents, e.g., amino acids, were present creating the required conditions to activate ferrate.

Contaminant Removal

Elimination of CBZ by ferrate with or without proline was initiated by mixing equal solution volumes of 10.0 mL, and the final pH values of reaction solutions (10.0 mM borate buffer) were kept at $9.00\pm0.05$. The concentration of ferrate was maintained at 100.0 µM, and the ratios of [proline]:[ferrate] in the system varied from 0 to 2.0 for aqueous removal of CBZ (5.0 µM). After certain reaction time, a 20.0 µL NH$_2$OH solution (1 M, [NH$_2$OH]: [ferrate]=10.0) was added to quench the reactions. Samples were transferred into high performance liquid chromatography (HPLC) vials and subsequently analyzed using the HPLC method. Each treatment was performed with triplicates and the mean removal values were reported.

Results and Discussion

Figure 2:
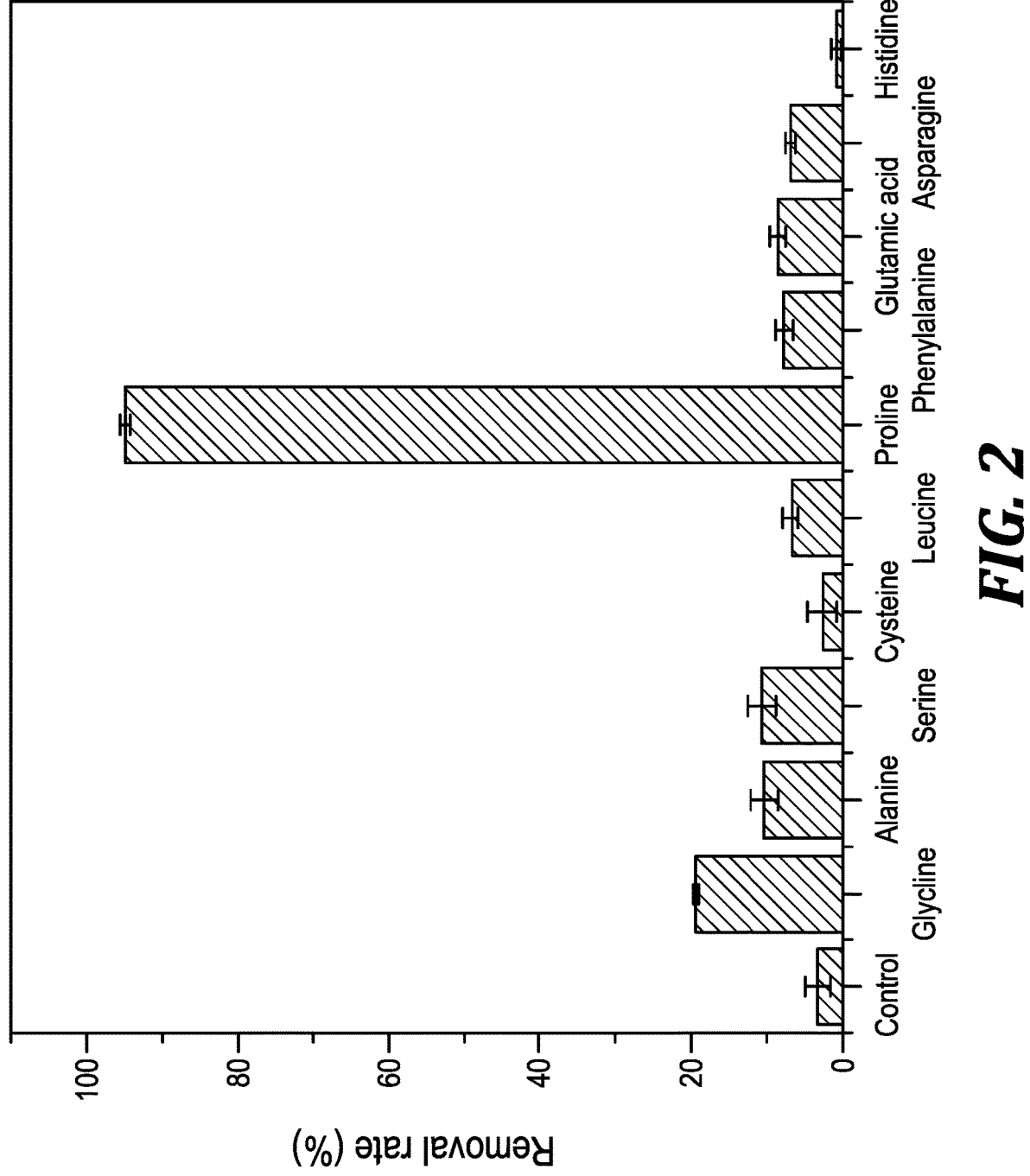
FIG. 2 shows the removal rate of Carbamazepine (CBZ) by Fe(VI) with or without the 10 different amino acids. (Experimental conditions: [CBZ]=5.0 μM, [ferrate]=100.0 μM, [amino acid]=100.0 μM, pH 9.0 (10.0 mM borate buffer), reaction time=1 min).

Preliminary experiments were conducted to see the influence of amino acids (100.0 µM) on removal of CBZ (5.0 µM) by ferrate (100.0 µM) at pH 9.0 (10.0 mM borate buffer) after 1 min of oxidation. In these experiments, the solution of selected amino acids (FIG. 1) was mixed with CBZ, followed by addition of ferrate. Removal of CBZ under the experimental conditions is shown in FIG. 2. Unexpectedly, the enhanced removal of CBZ was seen only when proline was present in the mixed solution, as compared to the oxidation of CBZ by ferrate only (i.e., control). Other amino acids had no such enhancement. This was surprising because the amino acids containing the same functional groups, i.e., amino and carboxylate did not show significant ferrate activation. The role of structure of amino acids may have a significant role in causing the enhanced removal of recalcitrant contaminants, i.e., CBZ, by ferrate.

Figure 3A:
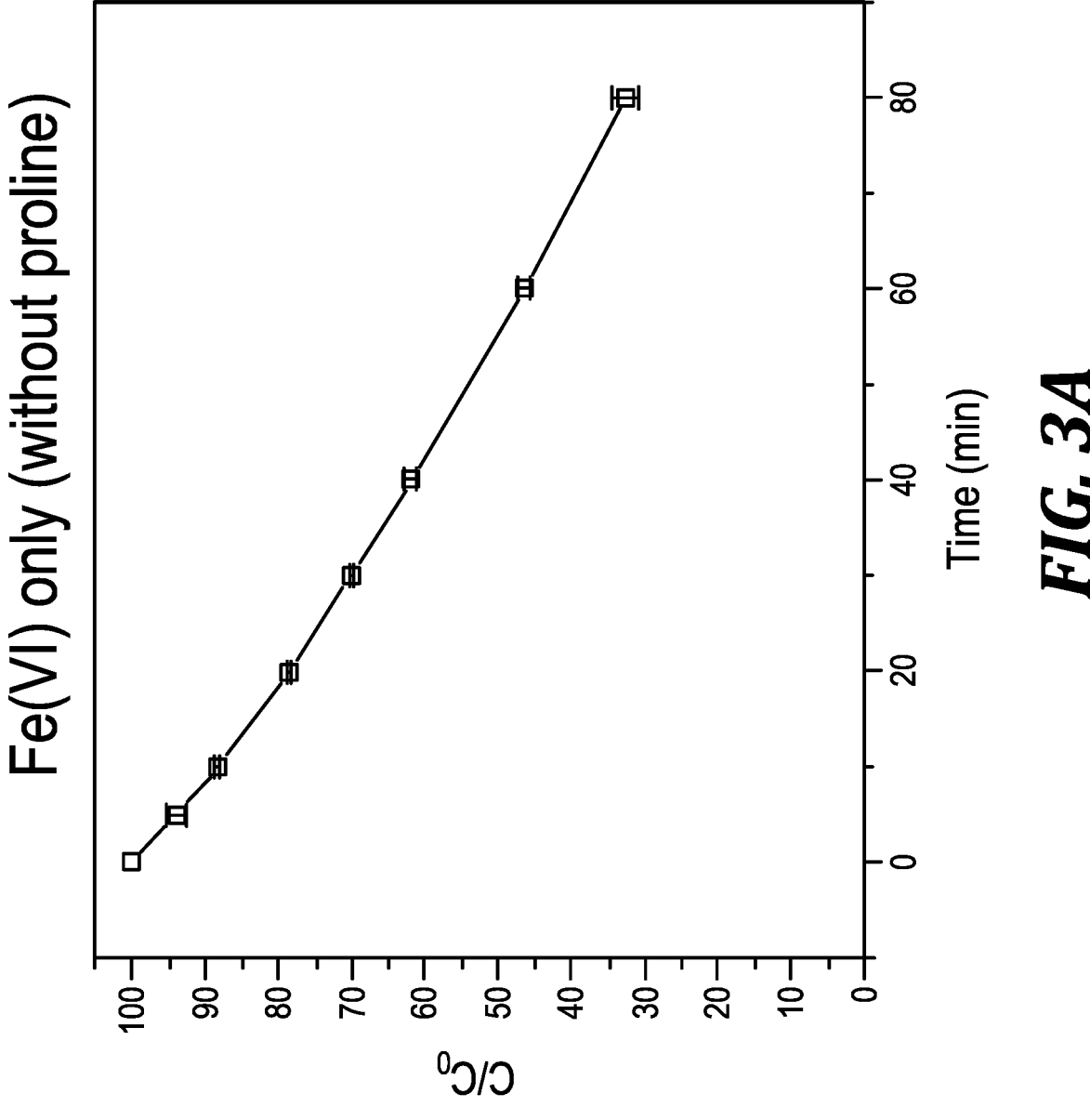
FIGS. 3A and 3B show removal of Carbamazepine (CBZ) by ferrate only (3A) and ferrate/proline system (3B). (Experimental conditions: [CBZ]=5.0 μM, [ferrate]=100.0 μM, [proline]=25.0, 50.0, 100.0, and 200.0 μM, pH 9.0 (10.0 mM borate buffer)).

Next, the concentration of proline in the mixed solution was varied by keeping the concentration of ferrate as constant and then removal of CBZ was monitored at pH 9.0 as a function of time. The molar ratio of proline to ferrate ranged from 0.25 to 2.0. Results are presented in FIG. 3. Without proline (or activator), ferrate took 80 min to remove 70% of the contaminant (FIG. 3A). However, when proline was used, the oxidation efficiency of ferrate increased dramatically and 70% removal of CBZ could be seen only in 1 min. Complete removal of CBZ by activated ferrate was achieved in 1.5 min (or 90 s).

Figure 3B:
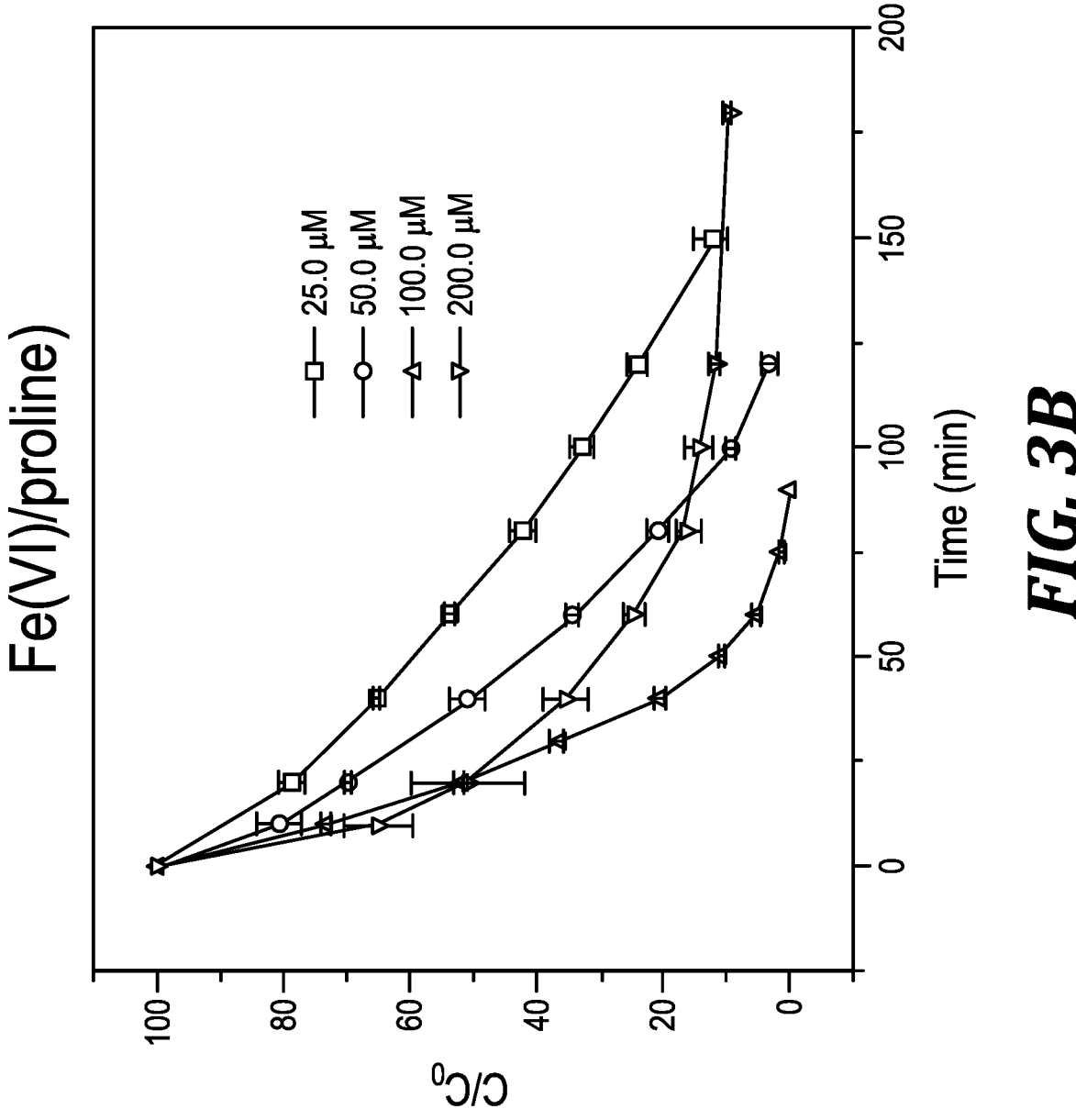
Figure 4:
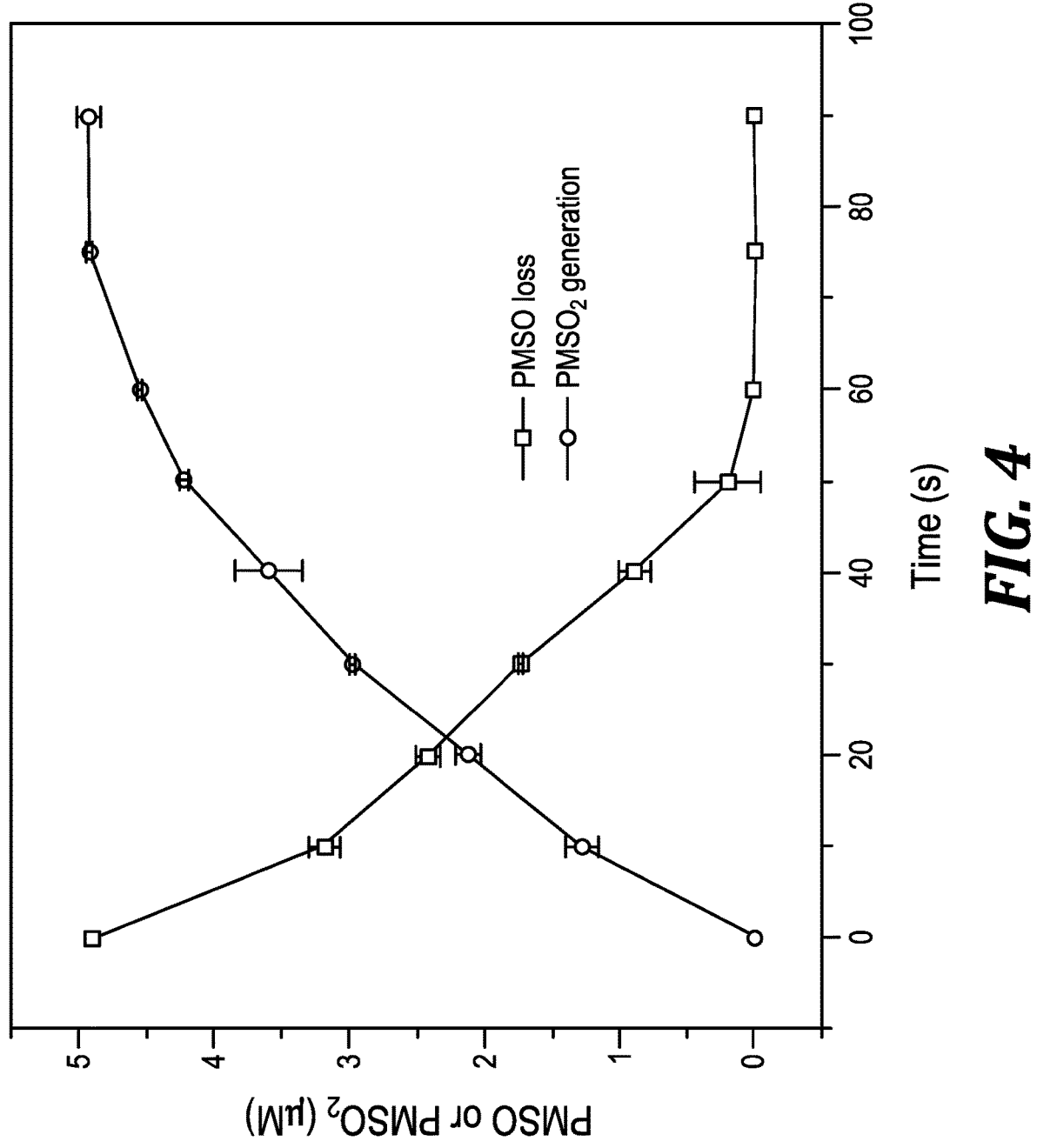
FIG. 4 is a graph of oxidation of methyl phenyl sulfoxide (PMSO) by activated ferrate (Experimental conditions: [PMSO]=5.0 uM, [Fe(VI)]=100.0 uM, [proline]=100.0 uM, pH=9.0)

The oxidation of CBZ increased up to 100% within 90 s at the molar ratio of 1.0 and then decreased when the molar ratio became 2.0 (FIG. 3B). The results suggested that not only the structure but also the molar ratio of proline to ferrate influenced the removal of CBZ. Significantly, results of FIG. 3 indicate the optimum molar ratio of activator (i.e., proline) to ferrate is pivotal to see the maximum removal of the recalcitrant contaminant like CBZ.

SUMMARY

Certain compounds such as amino acids comprising secondary amino groups, e.g., proline, can act as the activator to produce "activated ferrate" from the ferrate that can efficiently oxidize recalcitrant contaminants such as CBZ. The activator, when mixed with ferrate in a certain molar ratio, can achieve complete removal of the contaminant at a substantially shorter time than that required to remove the contaminant by a non-activated ferrate. Ferrate activators comprising secondary amino groups, such as proline, can also be used to achieve rapid and efficient inactivation of bacteria and viruses. Results obtained herein have implication in terms of providing some newer ferrate activators, for example, compounds comprising secondary amino groups, such as compounds structurally similar to proline. These activators can be also present (e. g, covalently attached) on solid supports like glass, polymers, and metal-organic frameworks, allowing generation of activated ferrate by contacting a composition comprising a ferrate precursor with such supports.

While illustrative embodiments have been illustrated and described, it will be appreciated that various changes can be made therein without departing from the spirit and scope of the invention.

The invention claimed is:

1. An activated ferrate composition comprising:
(a) one or more compounds comprising a secondary amino group, wherein the one or more compounds comprising the secondary amino group is an amino acid comprising a secondary amino group, and wherein the amino acid comprising the secondary amino group is proline; and
(b) ferrate.

2. The activated ferrate composition of claim 1, wherein the composition is an aqueous solution.

3. The activated ferrate composition of claim 1, wherein the concentration of ferrate is between about 0.001 wt % and about 5.0 wt %.

4. The activated ferrate composition of claim 1, further comprising a disinfectant selected from sodium hypochlorite, chloramine, quaternary alkylamines, and combinations thereof.

5. The activated ferrate composition of claim 1, further comprising one or more surfactants.

6. A method of reducing the concentration of one or more contaminants in a contaminated fluid comprising contacting the fluid with the activated ferrate composition of claim 1.

7. The method of claim 6, wherein the concentration of ferrate in the activated ferrate solution is from about 0.001 wt % to about 5.0 wt %.

8. The method of claim 6, wherein the activated ferrate composition comprises ferrate and proline.

9. The method of claim 8, wherein the concentration of proline in the activated ferrate solution is from about 0.0001 M to about 1.0 M.

10. The method of claim 6, wherein the one or more contaminants is *Escherichia coli, Staphylococcus aureus, Shigella flexneri, Salmonella typhimurium, Clostridium difficile* bacteria, *Clostridium difficile* spore, Rhinovirus, Norovirus, Zika virus, Ebola virus, *Aspergillus*, amoeba, helminthic egg, *Histoplasma*, or a combination thereof.

11. A method of disinfecting a surface comprising contacting one or more surfaces with the activated ferrate composition of claim 1.

12. The method of claim 11, wherein disinfecting the surface comprises killing one or more antibiotic-resistant microorganisms.

13. The method of claim 11, wherein disinfecting the surface comprises killing one or more antibiotic-resistant microorganisms.

14. The method of claim 11, wherein the surface comprises a material selected from the group consisting of glass, ceramic, metal, wallpaper, painted walls, and plastic.

15. The method of claim 6, wherein the one or more contaminants is a recalcitrant organic compound, a microorganism, or a combination thereof.

16. The activated ferrate composition of claim 1, wherein the molar ratio of the one or more amino acids comprising secondary amino group to ferrate is from about 0.25 to about 2.0.

17. The activated ferrate composition of claim 1, wherein the activated ferrate composition has a pH between about 5.0 and about 12.0, between about 7.0 and about 12.0, or between about 8.0 and about 10.0.

18. The activated ferrate composition of claim 1, wherein the concentration of ferrate is between about 0.001 wt % and about 1.0 wt %.

19. The activated ferrate composition of claim 2, wherein the aqueous solution comprises water.

20. The activated ferrate composition of claim 19, wherein the water is selected from the group consisting of undistilled water, non-deionized water, tap water, distilled water, deionized water, DDI water, and any combination thereof.

* * * * *